United States Patent
Mauldin, Jr. et al.

(10) Patent No.: US 9,002,080 B2
(45) Date of Patent: Apr. 7, 2015

(54) SINGULAR VALUE FILTER FOR IMAGING OR DETECTION

(71) Applicants: F. William Mauldin, Jr., Charlottesville, VA (US); John A. Hossack, Charlottesville, VA (US); Abhay V. Patil, Lawrence, MA (US)

(72) Inventors: F. William Mauldin, Jr., Charlottesville, VA (US); John A. Hossack, Charlottesville, VA (US); Abhay V. Patil, Lawrence, MA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 304 days.

(21) Appl. No.: 13/650,821

(22) Filed: Oct. 12, 2012

(65) Prior Publication Data

US 2013/0094729 A1    Apr. 18, 2013

Related U.S. Application Data

(60) Provisional application No. 61/546,129, filed on Oct. 12, 2011.

(51) Int. Cl.
*G06K 9/00* (2006.01)
*G06K 9/62* (2006.01)
*A61B 8/08* (2006.01)

(52) U.S. Cl.
CPC ............ *G06K 9/6247* (2013.01); *A61B 8/0891* (2013.01); *A61B 8/481* (2013.01); *A61B 8/5207* (2013.01)

(58) Field of Classification Search
None
See application file for complete search history.

(56) References Cited

U.S. PATENT DOCUMENTS

| | | |
|---|---|---|
| 7,402,136 B2 | 7/2008 | Hossack et al. |
| 7,699,776 B2 | 4/2010 | Walker et al. |
| 7,750,537 B2 | 7/2010 | Hossack et al. |

(Continued)

FOREIGN PATENT DOCUMENTS

| | | |
|---|---|---|
| WO | WO-03075769 A1 | 9/2003 |
| WO | WO-2004064620 A2 | 8/2004 |

(Continued)

OTHER PUBLICATIONS

Gallippi, C. M, et al., "BSS-based filtering of physiological and ARFI-induced tissue and blood motion", Ultrasound Med Biol., 29(11), (Nov. 2003), 1583-92.

(Continued)

*Primary Examiner* — Avinash J Yentrapati
(74) *Attorney, Agent, or Firm* — Schwegman Lundberg & Woessner, P.A.

(57) ABSTRACT

Apparatus or techniques can include obtaining information indicative of energy, such as ultrasonic energy, reflected from a tissue region, forming respective input matrices representative of the obtained information, the input matrices respectively comprising an ensemble-of-interest and at least one ensemble corresponding to a spatial location nearby a spatial location corresponding to the ensemble-of-interest, performing respective singular value decompositions on the respective input matrices to obtain respective sets of singular values corresponding to respective sets of singular vectors, obtaining respective output matrices including weighting a respective projection of a respective ensemble-of-interest onto at least one of the singular vectors included in a respective set of singular vectors, and, using the respective output matrices, at least one of determining a characteristic, or constructing an image, of at least a portion of the tissue region.

20 Claims, 13 Drawing Sheets
(6 of 13 Drawing Sheet(s) Filed in Color)

(56) References Cited

U.S. PATENT DOCUMENTS

| | | |
|---|---|---|
| 8,057,392 B2 | 11/2011 | Hossack et al. |
| 8,093,782 B1 | 1/2012 | Hossack |
| 2007/0016044 A1 | 1/2007 | Blalock et al. |
| 2008/0212887 A1* | 9/2008 | Gori et al. .............. 382/248 |
| 2009/0263001 A1* | 10/2009 | Ding et al. .............. 382/131 |
| 2010/0063399 A1 | 3/2010 | Walker et al. |
| 2010/0168578 A1 | 7/2010 | Garson, Jr. |
| 2010/0268086 A1 | 10/2010 | Walker et al. |
| 2010/0331686 A1 | 12/2010 | Hossack et al. |
| 2011/0137175 A1 | 6/2011 | Hossack et al. |
| 2012/0029356 A1 | 2/2012 | Hossack et al. |
| 2012/0163691 A1* | 6/2012 | Walker et al. .............. 382/131 |
| 2012/0263365 A1* | 10/2012 | Ding et al. .............. 382/131 |
| 2013/0094729 A1* | 4/2013 | Mauldin et al. .............. 382/128 |

FOREIGN PATENT DOCUMENTS

| | | |
|---|---|---|
| WO | WO-2004065978 A2 | 8/2004 |
| WO | WO-2008154632 A2 | 12/2008 |
| WO | WO-2009055720 A1 | 4/2009 |
| WO | WO-2010021709 A1 | 2/2010 |
| WO | WO-2011011539 A1 | 1/2011 |

OTHER PUBLICATIONS

Kruse, D. E, et al., "A new high resolution color flow system using an eigendecomposition-based adaptive filter for clutter rejection", IEEE Transactions on Ultrasonics, Ferroelectrics and Frequency Control, 49(10), (2002), 1384-1399.

Mauldin, F. W, et al., "Robust motion estimation using complex principal components", 2009 IEEE International Ultrasonics Symposium (IUS), (2009), 2429-2432.

Mauldin, F. William, et al., "The Singular Value Filter: A General Filter Design Strategy for PCA-Based Signal Separation in Medical Ultrasound Imaging", IEEE Transactions on Medical Imaging, 30(11), (Nov. 2011), 1951-1964.

Patil, A. V, et al., "Dual frequency method for simultaneous translation and real-time imaging of ultrasound contrast agents within large blood vessels", Ultrasound Med Biol., 35(12), (Dec. 2009), 2021-30.

Yu, A., et al., "Eigen-based clutter filter design for ultrasound color flow imaging: a review", IEEE Transactions on Ultrasonics, Ferroelectrics and Frequency Control, 57(5), (2010), 1096-1111.

Yu, A., et al., "Single-ensemble-based eigen-processing methods for color flow imaging—Part II. The matrix pencil estimator", IEEE Transactions on Ultrasonics, Ferroelectrics and Frequency Control, 55(3), (2008), 573-587.

* cited by examiner

SINGULAR VALUE FILTER FOR IMAGING OR DETECTION

CLAIM OF PRIORITY

This patent application claims the benefit of priority, under 35 U.S.C. Section 119(e), to Mauldin et al., U.S. Provisional Patent Application Ser. No. 61/546,129, entitled "Singular Value Filter System and Related Method," filed on Oct. 12, 2011, which is hereby incorporated by reference herein in its entirety.

STATEMENT REGARDING FEDERALLY SPONSORED RESEARCH OR DEVELOPMENT

This invention was made with government support under R01EB001826 awarded by the National Institutes of Health (NIH). The government has certain rights in the invention.

BACKGROUND

Filtering can be performed by decomposition (e.g., projection) of signals along a new set of bases. Such filtering can be used for image enhancement, such as to process echo information to reject artifacts such as clutter or to enhance or separate information of interest from other data. In this manner, the original echo information can be re-expressed along a new coordinate system such that the unwanted information (e.g., clutter) and the signal of interest are separated using the different bases. Bases describing a non-desirable source signal can be suppressed or rejected, and bases describing a desirable source signal can be enhanced or retained.

Such filtering techniques can be classified using information about the how the new bases are determined, such as including a priori determination of bases or adaptive determination of bases. One a priori approach is the Discrete Fourier Transform (DFT) where the bases are defined as complex exponentials without regard to the underlying data being filtered. Such a DFT approach can be used for zonal frequency-based filtering, such as established by a finite impulse response (FIR) filter topology, or an infinite impulse response (IIR) filter topology. Such zonal frequency-based filtering can be used for clutter rejection in applications such as blood vessel wall filtering for blood flow imaging.

However, such DFT-based methods suffer when the frequency characteristics of the non-desirable and desirable signal components overlap. Moreover, in medical ultrasound imaging applications, the non-desirable and desirable signal characteristics can often shift dramatically both space and time due motion, changes in physiology, or spatial variation in tissue structure.

OVERVIEW

In one approach, an adaptive framework for determining basis functions can include principal component analysis (PCA), which can also be referred to as a discrete Karhunen-Loeve Transform (KLT). In such a PCA-based approach, the basis functions can be determined adaptively using information about statistical properties of the input data. Such PCA-based techniques can be used for a variety of applications in medical ultrasound including clutter reduction in blood flow estimation, displacement estimation, displacement profile filtering, beamforming, or classification of tissue response to acoustic radiation force, for example. However, the present inventors have recognized, among other things, that existing PCA-based approaches can be unable to select appropriate filter coefficients in an automated manner. Moreover, strict thresholding of basis function weighting (e.g., either completely retaining or completely rejecting a basis in a binary manner) can cause artifacts or does not achieve desirable filtering results.

Accordingly, the present inventors have developed apparatus and techniques to implement singular value filtering (SVF) that can include basis function weightings that one or more of vary continuously without discontinuity or can be adaptively determined using information about the underlying signal to be filtered. For example, such an SVF technique can adaptively determine one or more weighting functions using information about one or more singular values of a respective ensemble used for determining a pixel value or characteristic of a tissue region being analyzed.

Generally, apparatus or techniques described in the examples herein can include a singular value filter (SVF) technique that can be used to improve image quality or reduce errors from quantitative measurements extracted from received echo information, such as ultrasound echo information indicative of displacement or velocity. In an example, an SVF approach can be used reject clutter artifact for improved image quality or for isolation of a microbubble signal or other desired signal, such as for improved ultrasound-based targeted molecular imaging. Other applications can include motion characterization of acoustic targets or measurement of molecular probe specificity and binding strength.

According to various examples, apparatus or techniques can include obtaining information indicative of energy, such as ultrasonic energy, reflected from a tissue region, forming respective input matrices representative of the obtained information, the input matrices respectively comprising an ensemble-of-interest and at least one ensemble corresponding to a spatial location nearby a spatial location corresponding to the ensemble-of-interest, performing respective singular value decompositions on the respective input matrices to obtain respective sets of singular values corresponding to respective sets of singular vectors, obtaining respective output matrices including weighting a respective projection of a respective ensemble-of-interest onto at least one of the singular vectors included in a respective set of singular vectors, and, using the respective output matrices, at least one of determining a characteristic, or constructing an image, of at least a portion of the tissue region.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
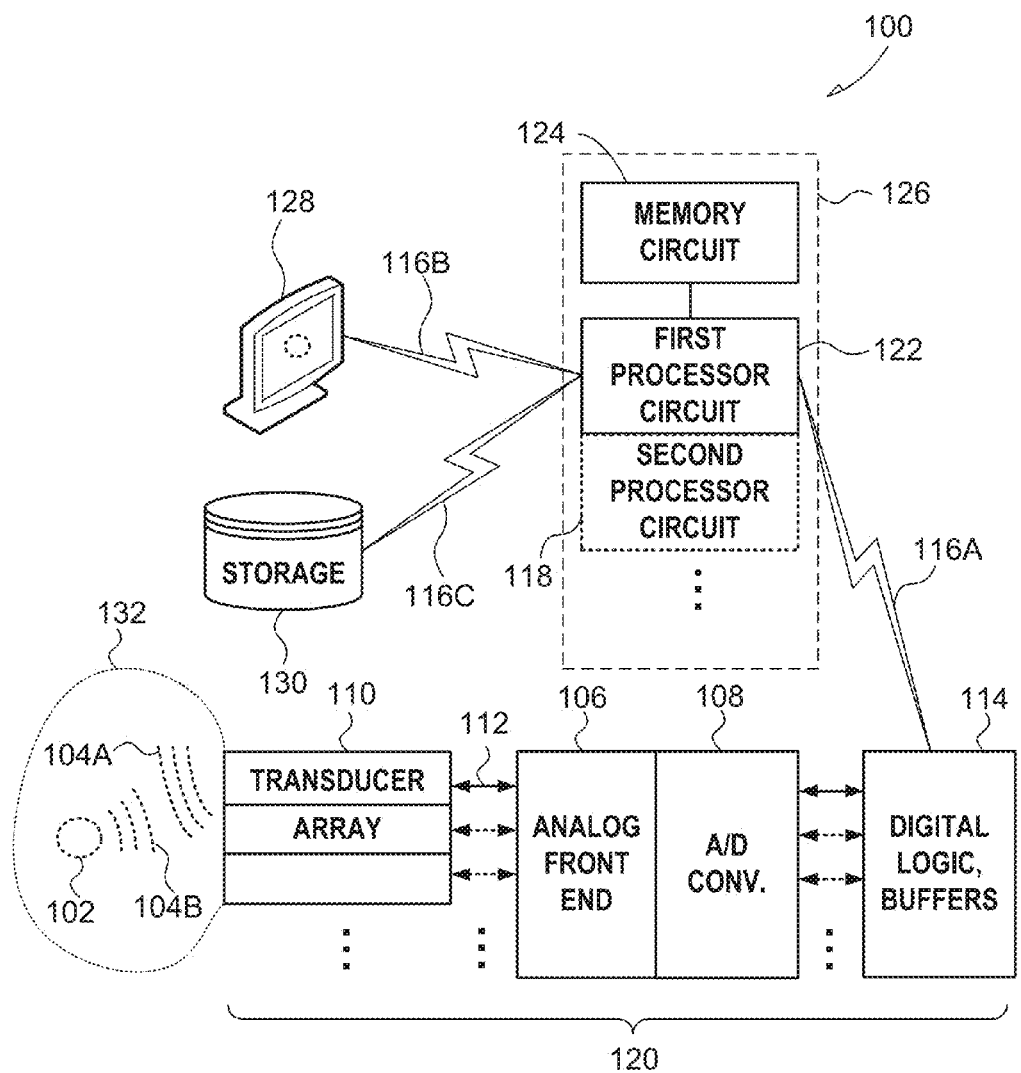
FIG. 1 illustrates generally an example of a system, such as can be used for echo-imaging using a singular value filtering technique.

FIG. 1 illustrates generally an example of portions of a system 100 that can include an ultrasonic imaging system, and portions of an environment in which the system 100 can be used. Such a system can be used to perform a singular value filtering (SVF) technique.

In an example, the system 100 can include a first processor circuit 122, a memory circuit 124, a display 128, a storage unit 130, one or more transducers 110, an analog front-end 106 coupled to an array of transducers 110, such as via a bus 112, one or more analog-to-digital (A/D) converters 108, and a digital logic circuit 114 such as including one or more buffers. In FIG. 1, one or more of the memory circuit 124, the first processor circuit 122, or one or more additional processor circuits such as a second processor circuit 118 can be included in a computer system 126. Such as computer system 126 can include a hand-held or tablet computer, a desktop computer, a laptop computer, a computer server, or a combination of one or more general purpose or special purpose computers, such as configured to obtain ultrasonic echo information from a transducer block 120, such as via a wired or wireless communication link 116A.

In an example, a region of interest 132 can include one or more actual targets such as a first target 102. The region of interest 132 can be excited (e.g., insonified, etc.) such as using energy provided by the transducer array 110, such as under the control of the first processor circuit 122. For example, a transmitted ultrasonic energy 104A can propagate through the region of interest 132, and a portion of the transmitted energy 104A can be scattered or reflected by one or more targets, such as the first target 102, to provide an echo 104B. The transducer array 110 can be configured to receive a portion of the echo 104B. The analog front end circuit 106 can be configured for processing the resulting transduced echo signal, such as conditioning, delaying, filtering, or otherwise processing the received echo 104B.

Signal processing can further include converting the received energy from an analog signal representation into a digital representation, such as using one or more of the analog-to-digital converters 108. Such a digital representation can include real-valued information representative of the received energy, or a complex-valued representation that can include real or imaginary parts.

In an array example, one or more of the bus 112, the A/D converters 108, or the digital logic circuit 114 can include a respective channels corresponding to respective transducers included in the array of transducers 110. For example, a transducer in the array of transducers 110 can be coupled to a respective portion of the analog front end 106, including a respective analog-to-digital converter, or buffered by a respective digital buffer. In an array example, one or more portions of the analog front end 106, the one or more analog-to-digital converters 108, or the digital logic circuit can be commonly-shared between two or more transducers, such as to simplify the construction of an ultrasonic transducer assembly 120, such as multiplexed over time (e.g., within a single transmission or across multiple transmissions).

In an example, the storage unit 130 can be included as a portion of a general or special purpose computer, such as the computer system 126. For example, ultrasonic echo information obtained from the ultrasonic transducer assembly 120 can be stored on the storage unit 130, such as transferred to the storage unit 130 via a wired or wireless communication link 116C. In an example, the ultrasonic echo information can be processed, such as to reconstruct an image including a representation showing the target 102. Such processing need not occur using the same computer system 126 as can be used to control the transducer assembly 120.

One or more techniques such as included in the examples below can be machine-implemented or computer implemented, such as performed by the system 100 corresponding to instructions stored in one or more of the memory circuit 124 or the storage unit 130, or stored or obtained from one or more other locations. In an example, one or more of the memory circuit 124 or the storage unit 130 can include a processor-readable medium, such as comprising instructions that when performed by the first or second processors 122, 118, cause the processors or system 100 to perform one or more of the techniques included in the examples discussed below and in relation to the other FIGS.

In an example, the transducer array 110 can be configured to insonify the region of interest 132 using ultrasonic energy, and the region of interest can include a tissue region (e.g., a blood vessel region, or one or more other locations). In such an illustrative tissue imaging example, the target 102 can represent a portion of a blood vessel (e.g., a wall, or a lumen including blood), a molecular species such as including one or more gas bubbles, or generally, any inhomogeneity or scatterer in the region of interest 132. In such an illustrative tissue imaging example, reflected energy can include an ultrasonic echo 104B that can be digitized and converted to an echo data set provided to the computer system 126. For example, the computer system 126 can then construct a representation (e.g., a B-mode representation) such as for presentation as an image using the display 128.

The system 100 of FIG. 1 can be used with the examples discussed below. For example, the system 100 can be used for one or more of ultrasound imaging artifact reduction or ultrasound-based targeted molecular imaging, such as can include a singular value filtering technique.

Figure 2:
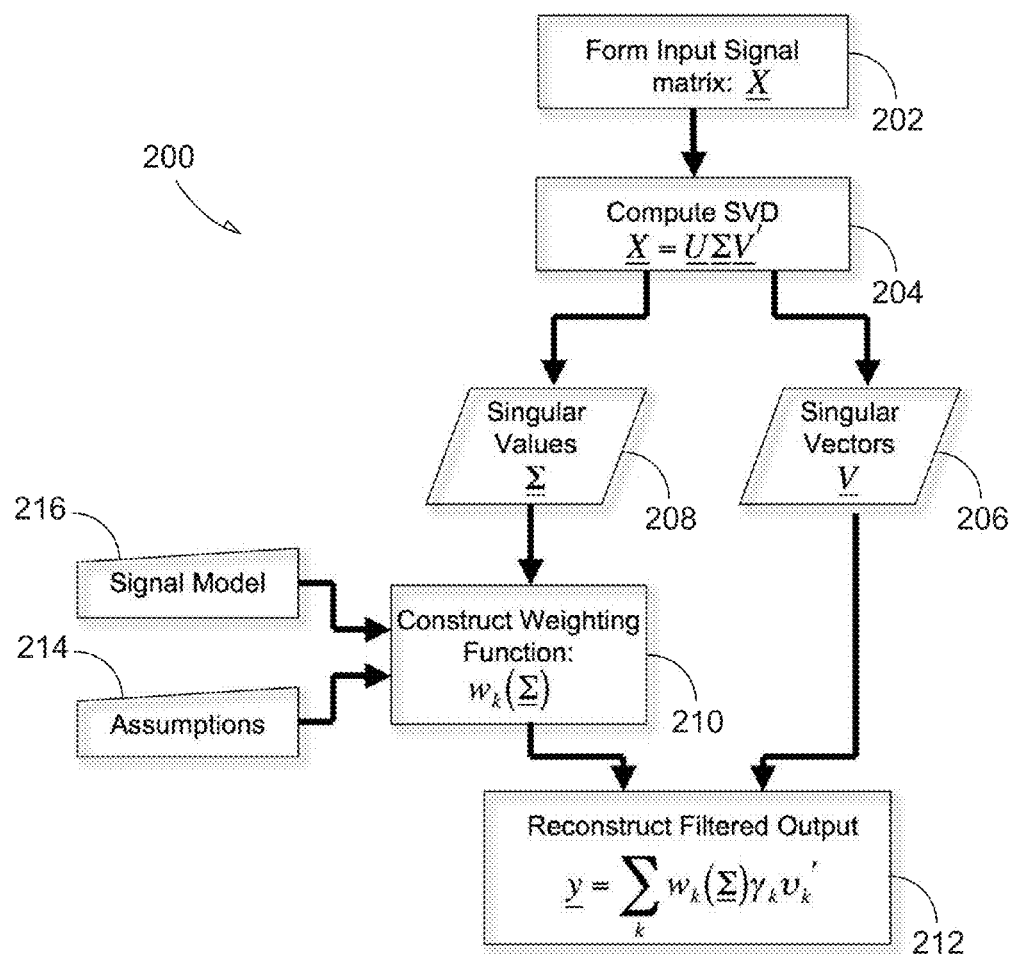
FIG. 2 illustrates generally an example that can include a portion of a singular value filtering technique.

FIG. 2 illustrates generally an example 200 that can include at least a portion of a singular value filtering (SVF) technique. At 202, the SVF approach can include forming an input signal matrix that can be represented by X, such as having dimensions M×N. For example, the respective rows of X can correspond to ensembles of echo data (e.g., complex-valued echo data) that can immediately surround an ensemble of interest, $x_{M/2}$ (e.g., of dimension 1×N).

At 204, the SVF technique can include performing a singular value decomposition (SVD) of respective input matrices, such as performing an SVD on a respective input matrix:

$$X = U \underline{\Sigma} V'  \qquad \text{EQN. 1}$$

where U can represent a matrix with left singular vectors corresponding to the eigenvectors of XX' and V can represent a matrix of right singular vectors corresponding to the eigenvectors of the autocorrelation matrix X'X=R. The right singular vectors can indicate directions of maximum variance through a "slow time" (e.g., frame length) dimension, as compared to a "fast time" dimension (e.g., depth dimension), and thus describe one or more motion characteristics of underlying scatterers.

At 208, singular values associated with each singular vector can be obtained from the diagonal entries of matrix $\underline{\Sigma}$, where singular values can be real and positive and typically arranged in descending order such that $\underline{\Sigma}_{11} \geq \underline{\Sigma} \geq \ldots \leq \underline{\Sigma}_{NN}$, corresponding to singular vectors, V, that can be provided at 206. Such singular values can be indicative of the amount of variance in the input matrix X accounted for by a corresponding singular vector. Thus, the first singular vector can account for the greatest source of variability in the data, the second singular vector can account for the second most significant source of variability, and so forth. Each column of input matrix X can be mean reduced such that every column in X can have a zero mean, such as before performing other processing.

At 210, a weighting function can be determined, such as adaptively determined using information about one or more singular values that can be provided at 208 in the matrix $\underline{\Sigma}$. Generally, filter design in SVF can include determination of a weighting function that relates a singular value spectrum to respective weighting coefficients. This weighting function can be adaptively determined using information such as a signal model 216 or assumptions 214 concerning the imaging environment. In an illustrative example of ultrasound clutter rejection, the signal model 216 for an observed ensemble of echo data x (dim 1×N) can be represented by:

$$x = \begin{cases} \underline{s} + \underline{c} + \underline{n} & \text{(regions of artifact)} \\ \underline{s} + \underline{n} & \text{(regions of tissue)} \end{cases} \qquad \text{EQN. 2}$$

where s, c, and n can represent source signals of the same dimensions as x, such as respectively representing echoes from tissue of interest, a clutter artifact, and white (e.g., electronic) noise respectively. In this example, an SVF technique can be used in clutter rejection to attenuate or reject PCA basis functions that describe clutter artifact.

The weighting function for such clutter reduction can be constructed using two assumptions 214. First, in local spatial regions of clutter artifact, the clutter artifact signal can be assumed to dominate. Second, clutter artifact is assumed to exhibit less motion and decorrelation, and thus a higher $\Sigma_{11}/\text{Tr}(\Sigma)$ ratio than surrounding desirable tissue signal. Such a ratio can be defined as a ratio (or other relative indication of information) of the first singular value ($\underline{\Sigma}_{11}$) to the sum of singular values ($\text{Tr}(\underline{\Sigma})$) determined from respective ensembles of echo data.

Many different weighting functions can be constructed in agreement with a signal model or assumptions. In a clutter reduction example, a modified sigmoidal function can be used to adaptively determine the filter weighting coefficients:

$$w_k(\Sigma_{kk}/Tr(\Sigma)) = 1 - \frac{1}{1 + e^{-\alpha(\Sigma_{kk}/Tr(\Sigma) - \tau)}} \qquad \text{EQN. 3}$$

where $\tau$ and $\alpha$ can represent weighting function parameters that can be used to adjust a $\Sigma_{kk}/\text{Tr}(\Sigma)$ cutoff threshold or weighting function slope, respectively.

Other weighting functions can be shaped using one or more of a Gaussian, Hamming, or Hann windowing function. The weighting function can take the form of a notch or band pass filter, such as to enhance or attenuate signal components associated with a specified level or range of motion complexity (e.g., axial shift or decorrelation). For example, a weighting function can be defined as:

$$w_k(\Sigma) = e^{-\frac{(f(\Sigma) - \mu)^2}{2\sigma^2}} \qquad \text{EQN. 4}$$

where $\mu$ can represent a mean, and $\sigma$ can represent a standard deviation of the weighting function envelope, and $f(\Sigma)$ can represent a function of the singular value spectrum, such as $\Sigma_{kk}/\text{Tr}(\Sigma)$. In this manner, the weighting function changes adaptively in response to variation in the underlying ensembles, because such variation in the respective underlying ensembles results in different singular values for respective singular value determinations.

At 212, such as following construction of the weighting function at 210, an SVF-filtered ensemble (such as for image reconstruction) can be represented by:

$$\underline{y} = \sum_{k=1}^{N} w_k(\Sigma_{kk}/Tr(\Sigma))\gamma_k \underline{v}_k \qquad \text{EQN. 5}$$

where y can represent an SVF-filtered output, $\gamma_k$ can represent a projection of the ensemble of interest $x_{M/2}$ onto the kth PCA basis function, $v_k$ (e.g., using an inner product):

$$\gamma_k = x_{M/2} v_k' \qquad \text{EQN. 6}$$

The same weighting function need not be used for every basis function. For example, different weighing functions can be assigned for respective filter coefficients (e.g., terms in the summation of EQN. 5). For example, the weighting function can be a high-pass configuration (e.g., higher weightings for higher $\Sigma_{11}/\text{Tr}(\Sigma)$) for one or more components associated with larger singular values, similar to EQN. 3, or a low-pass configuration for one or more components associated with less significant singular values. For example, a signal model similar to the clutter artifact example can be used, but instead of attenuating clutter, clutter can be enhanced and the tissue signal can be attenuated. Such an example can include weighting functions such as:

$$w_1(\Sigma_{11}/Tr(\Sigma)) = 1 - \frac{1}{1 + e^{-\alpha(\Sigma_{11}/Tr(\Sigma))^{-\tau}}} \quad \text{EQN. 7}$$

$$w_2(\Sigma_{22}/Tr(\Sigma)) = 1 - \frac{1}{1 + e^{-\alpha(\Sigma_{22}/Tr(\Sigma))^{-\tau}}} \quad \text{EQN. 8}$$

$$w_3(\Sigma_{33}/Tr(\Sigma)) = 1 - \frac{1}{1 + e^{-\alpha(\Sigma_{33}/Tr(\Sigma))^{-\tau}}} \quad \text{EQN. 9}$$

In an example, a high-pass or low-pass filter shape can be specified or retained, and a change in threshold τ or slope α can be specified as a function of the index of the filter coefficient, $w_1$ through $w_N$.

Figure 3:
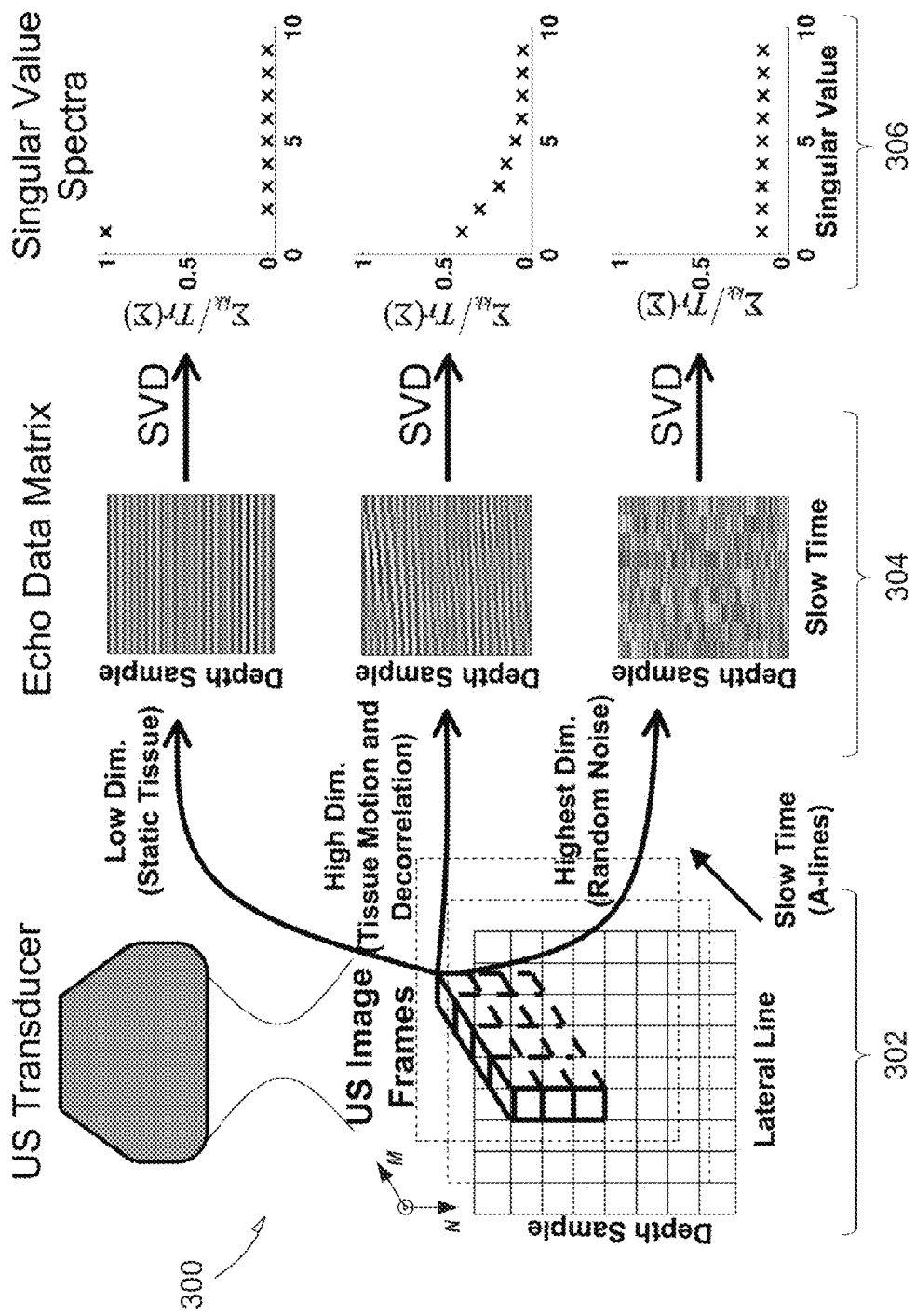
FIG. 3 illustrates generally an example that can include a portion of a singular value filtering technique, such as including forming an input matrix and performing a singular value decomposition on the input matrix.

FIG. 3 illustrates generally an example 300 that can include a portion of a singular value filtering technique, such as including forming 304 a respective input matrix 302 and performing a singular value decomposition (SVD) 306 on the input matrix 302.

As discussed in FIG. 2, filtering using an SVF technique can include forming 304 respective input matrices including ensembles of echo data, performing SVD on the respective ensembles, such as ensembles corresponding to respective pixels in an image. An M×N window can be "slid" through the set of image frames (e.g., each frame can represent a time slice in "slow time" as shown in FIG. 3). The respective input matrices can include a dimension corresponding to "fast time" (e.g., a spatial dimension such as depth from a transducer face) that can be represented by M, and a dimension corresponding to "slow time" that can be represented by N.

The present inventors have recognized, among other things, that determining respective sets of PCA basis functions and filter coefficients for respective spatial locations of an image is advantageous as compared to determining a single set of basis function for an entirety of the image. Observations in the respective ensembles, X, can better approximate stationarity and basis functions can better adapt to local spatial variations in the ultrasound data.

In this manner, respective pixel locations can each be assigned singular vectors and singular values that correspond to the SVD result, such as when an ensemble of interest corresponding to a pixel of interest is placed at $x_{M/2,N/2}$ in X. The value of M can be determined, such as using an SVF kernel window length, and N can correspond to an SVF ensemble length. Pixel locations at the edge of the echo data set need not be filtered if the M×N window to form X lies temporally or spatially outside of the sampled echo values (e.g., at an image boundary). The input matrices (e.g., respective ensembles X) can be complex-valued, such as including information that can be represented using a real part or an imaginary part.

Figure 4A:
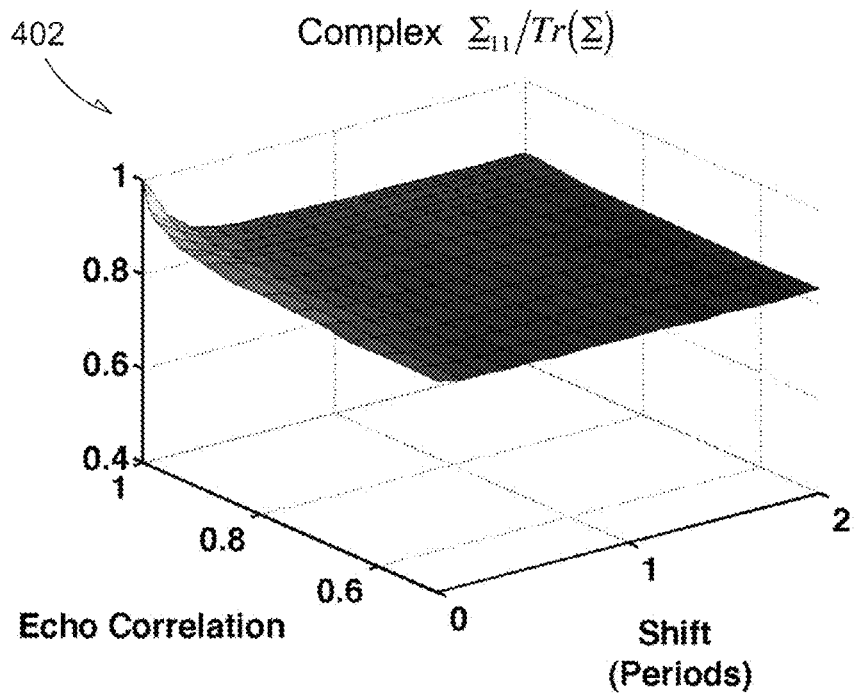
FIGS. 4A and 4B illustrate respective illustrative examples of a comparison between complex and real-valued singular value spectra, such as can be obtained using a simulation.
Figure 4B:
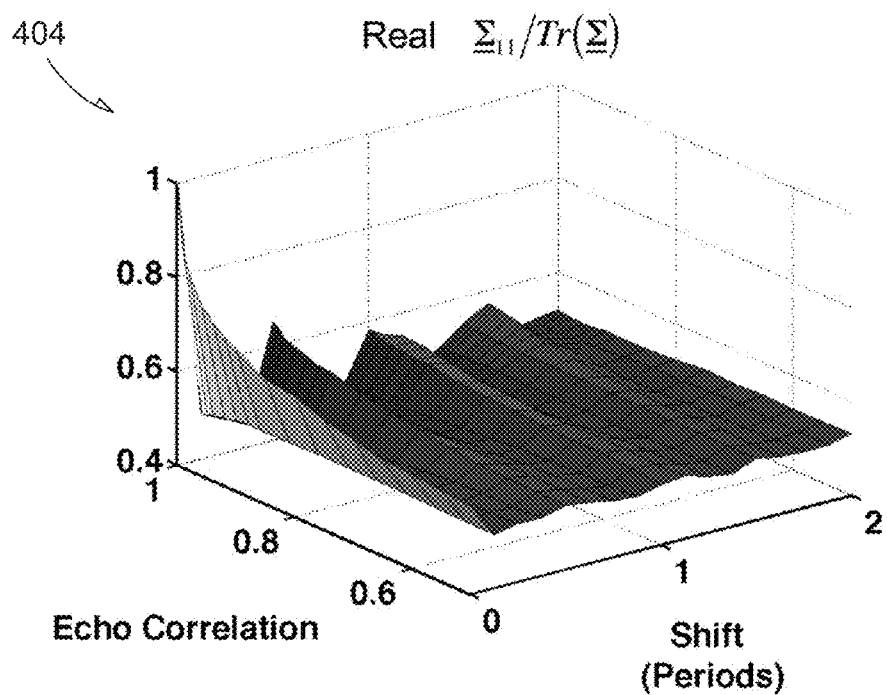

FIGS. 4A and 4B illustrate respective illustrative examples of a comparison between a complex-valued singular value spectrum 402 and real-valued singular value spectrum 404, such as can be obtained using a simulation. A ratio of the first singular value ($\Sigma$) to the sum of singular values ($\text{Tr}(\Sigma)$) can be simulated using FIELD II software and MATLAB (The Mathworks Inc., Natick, Mass., USA) from ensembles of echo data including complex echo data (in FIG. 4A) and real echo data (in FIG. 4B).

The singular value ratio $\Sigma/\text{Tr}(\Sigma)$ 402 resulting from the simulated complex echo data are monotonic with motion complexity (e.g., corresponding to an amount of decorrelation or motion between successive frames), whereas singular values from real data are not monotonic, such as due to singular value pairing. Singular value ratios $\Sigma_{11}/\text{Tr}(\Sigma)$ are generally much larger when estimated from complex data, indicating that the first complex PCA basis function generally describes a larger percentage of the variability in X than when PCA basis functions and the input matrix of echo data, X, are real.

An Illustrative example of parameters that can be used for obtaining the simulation of FIG. 4A are as follows, such as can obtained over 100 trials:

TABLE I

| Simulation Parameters | Default Values |
|---|---|
| Center Frequency | 5 MHz |
| Sampling Frequency | 40 MHz |
| Fractional Bandwidth | 50% |
| Tissue Echo Correlation | 0.98 |
| Artifact Echo Correlation | 1.0 |
| Tissue Displacement | 1 Period per A-line |
| Artifact Displacement | ⅛ Period per A-line |
| Ensemble Length | 9 A-lines |
| SVF Kernel Length | 3 Periods |
| SVF Weighting α Parameter | 30 |

Figure 5:
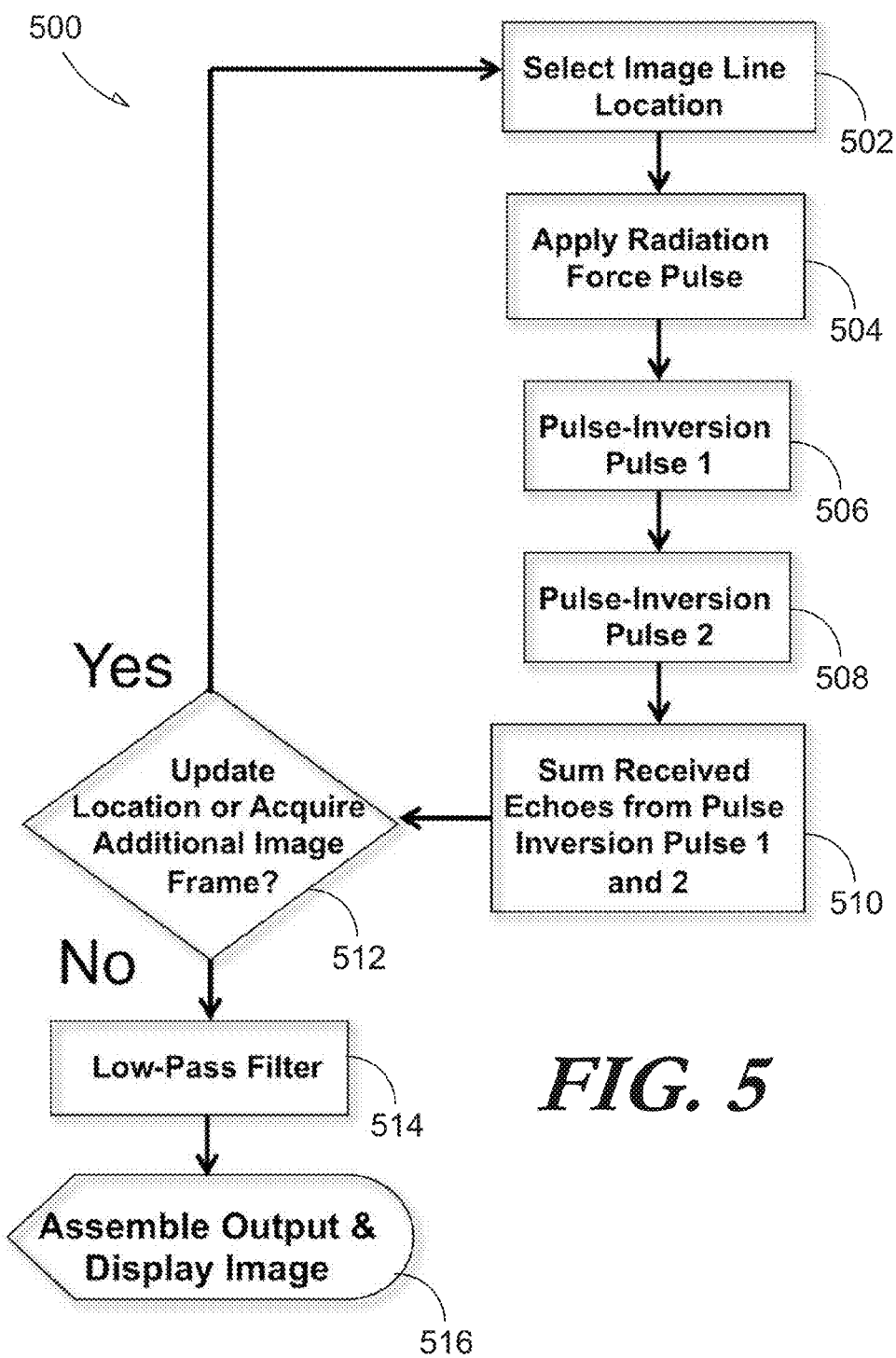
FIG. 5 illustrates generally a technique that can be referred to as a resonance stimulation and pulse inversion (RS-PI) technique, such as can include contrast pulse sequencing (CPS) and Doppler-based filtering, such as for blood-vessel imaging.

FIG. 5 illustrates generally a technique 500 that can be referred to as a resonance stimulation and pulse inversion (RS-PI) technique, such as can include contrast pulse sequencing (CPS) and Doppler-based filtering, such as for blood-vessel imaging.

Real-time acoustic radiation force-based techniques can be used for ultrasound-based targeted molecular imaging in vessels. Such techniques have generally been limited to demonstration in small vessels in vitro and in vivo. Real-time imaging can be achieved with such techniques, such as using a combination of multi-frequency imaging techniques and Doppler-based "slow-time" frequency filtering. In another approach, other techniques can include differentiating targeted microbubbles based on fracture characteristics, but such techniques generally do not provide information about microbubble adhesion over time during imaging, which is a significant limitation.

The approach of FIG. 5 can be used to image a vessel. The technique 500 can include selecting an imaging line location at 502, applying a radiation force acoustic pulse at 504, providing a first pulse-inversion pulse at 506, providing a second pulse inversion pulse at 508, summing received echo information from the respective first and second inversion pulses, updating to a new location or repeating 502-510 for an additional image frame, low-passing filtering the results at 514, and assembling an output at 516.

The efficacy of the technique 500 has been demonstrated ex vivo in porcine carotid arteries at physiologically relevant diameters and flow rates of human large vessels. However, the technique 500 can be limited in its achievable imaging sensitivity and specificity when used in real-world applications. Primarily, the pulse inversions at 506 or 508 and the frequency-based filtering at 514 steps can be corrupted when motion (e.g., physiological motion from breathing or vessel pulsations) occurs between subsequent ultrasound imaging pulses. Moreover, the signal components from adherent microbubbles and tissue structures, such as the vessel wall, exhibit substantial overlap in the frequency domain and thus, frequency-based filtering is largely ineffective at separating the two components. Such limitations of the approach of FIG. 5 can thus limit sensitivity and specificity performance, which can limit the usefulness of FIG. 5's techniques in applications with low microbubble concentration, high flow rates, or for use in vessels at greater imaging depths.

Figure 6:
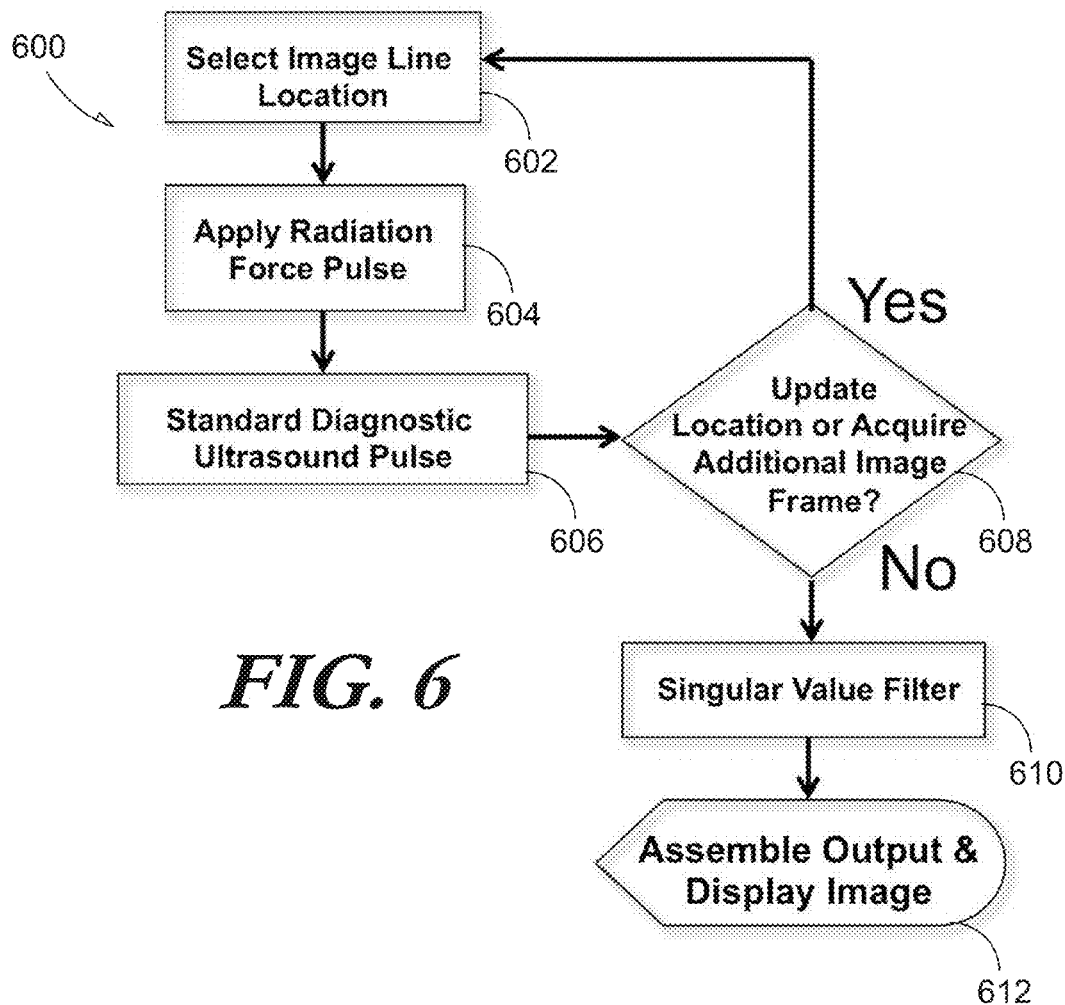
FIG. 6 illustrates generally an example that can include a technique for singular spectrum-base targeted molecular (SiSTM) imaging, such as can include a singular value filtering techniques as shown in the example of FIG. 3.

In another approach, in contrast to FIG. 5, FIG. 6 illustrates generally an example 600 that can include a technique for singular spectrum-base targeted molecular (SiSTM) imaging, such as can include a singular value filtering (SVF) technique as shown and described in the examples of FIGS. 2 and 3.

The SiSTM imaging technique cam include real-time ultrasound-based targeted molecular imaging that can use an SVF filtering technique, such as to differentiate adherent microbubbles from free microbubbles and tissue. Acoustic radiation force pulses can be used to increase efficiency of microbubble binding to desired receptor targets, such as to improve imaging contrast or determination of one or more characteristics such as motion.

The technique of FIG. 6 need not rely on non-linear characteristics of echo information from microbubbles or slow-time frequency-domain filtering, in contrast to techniques such as projection initialization plus IIR filtering (PI+IIR) or harmonic+IIR techniques. Instead, a SiSTM technique, such as shown in FIG. 6, can be used to separate signal components based on their respective singular spectrum signatures. Unlike performing pulse inversion, which generally includes multiple transmits per image line, a SiSTM technique can be performed using a single transmit event, such as enabling higher frame rates and avoiding limitations of approaches that use multiple pulses per line. Such multi-pulse approaches can be vulnerable to corruption arising from motion between transmit events.

As discussed in FIGS. 2 and 3, SVF can represent a generalized approach to linear signal separation where filter coefficients are assigned to respective principal component basis functions, such as weighted using an adaptively determined weighting function. Such a function can be adaptively determined using information obtained from the singular value spectrum.

In an illustrative example of targeted imaging, filter coefficients for the adaptively determined weighting functions can be constructed, such as using assumptions concerning respective source signals including the signal model:

$$x = \begin{cases} \underline{a} + \underline{t} + \underline{n} & \text{(regions of adherent bubbles)} \\ \underline{f} + \underline{n} & \text{(regions of free bubbles)} \\ \underline{t} + \underline{n} & \text{(regions of tissue)} \end{cases} \quad \text{EQN. 10}$$

where a, f, t, and n can represent source signals of the same dimensions as x, such as respectively representing echoes from adherent microbubbles, free microbubbles, tissue, and noise. Statistical assumptions concerning these source signals can be derived from known physical behaviors of the source signals. For example, the first assumption can include that microbubbles generate a greater magnitude of non-linear harmonic signal than tissue. The second assumption can be that free microbubbles possess greater motion and decorrelation characteristics than adherent microbubbles and tissue. Such assumptions are similar to a general rationale for real-time targeted molecular imaging strategies where non-linear signals can be enhanced via harmonic imaging or contrast pulse sequenced (CPS) techniques, where slow-time low pass filtering can be used to attenuation free microbubble signal.

In SVF, the singular spectrum data provides information relevant to both harmonic signal and motion characteristics. Rather than applying a combination of frequency filtering or CPS and frequency filtering as in other approaches, SiSTM can use the singular spectrum information from regions of echo data spanning 'fast time' and 'slow time' (e.g., an input matrix X, which can include multiple ensembles through depth), such as to isolate regions of the image corresponding to adherent microbubbles.

Figure 7A:
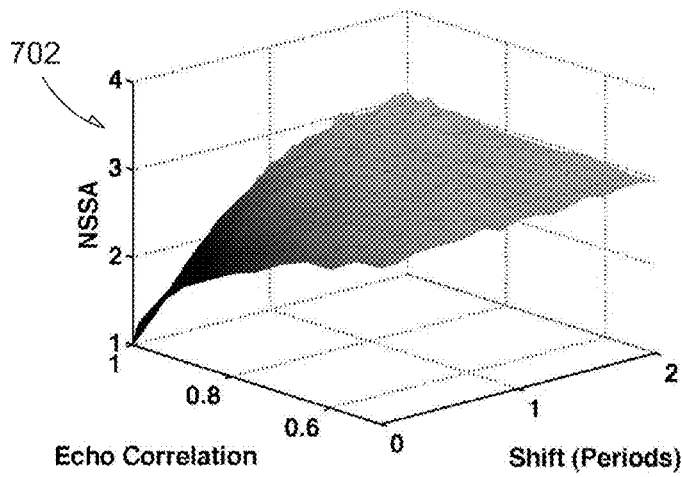
FIGS. 7A through 7C illustrate generally illustrative examples of a normalized singular spectrum area (NSSA), such as can be obtained as a function of echo correlation and axial displacement as shown in FIG. 7A, harmonic energy as shown in FIG. 7B, or differential motion as shown in FIG. 7C.
Figure 7B:
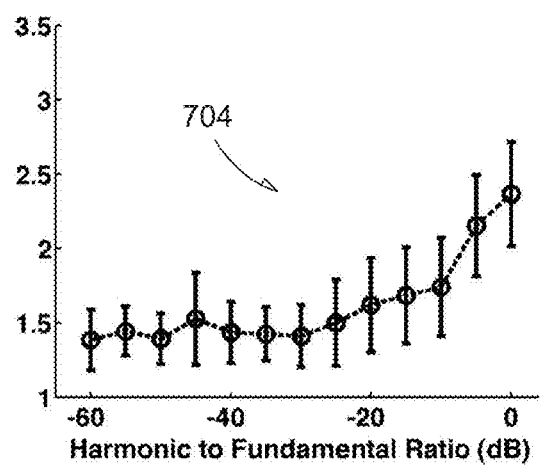
Figure 7C:
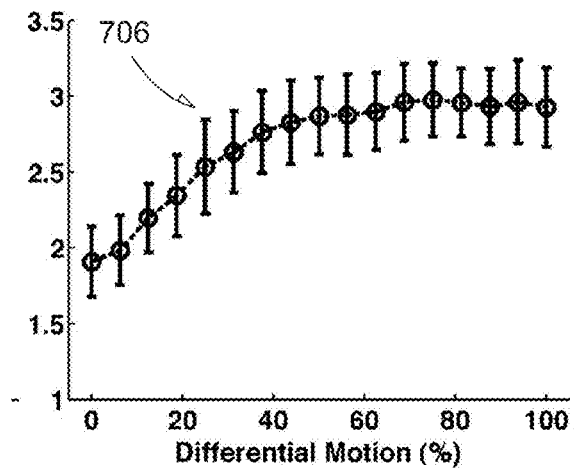

FIGS. 7A through 7C illustrate generally illustrative examples of a normalized singular spectrum area (NSSA), such as can be obtained as a function of echo correlation and axial displacement as shown in FIG. 7A, harmonic energy as shown in FIG. 7B, or differential motion as shown in FIG. 7C.

The illustrative examples of FIGS. 7A through 7C can be obtained via simulation using FIELD II software and MATLAB software. Respective ensembles of complex echo data can be used to form respective input matrices, such as the matrix X. A 'calc_scat' function in FIELD II can be used to calculate a received signal from a collection of scatterers.

NSSA can represent a metric that can be used to quantify a statistical dimensionality of received echo information using information about the echo information' singular spectrum, in dependence on motion, harmonic energy, or differential motion of ensembles of ultrasound data. Illustrative examples of NSSAs obtained via simulation are illustrated as a function of echo correlation and axial displacement 702, as a function of harmonic energy 704, and as a function of differential motion 706. Differential motion can be simulated by assigning displacements to scatterers with a Gaussian probability density function. Harmonics can be simulated by superimposing a 10 megahertz (MHz) generated ensemble onto 5 MHz ensemble data using the same set of acoustic scatterers.

NSSA can be represented as follows:

$$NSSA = \sum_{k=1}^{N} \Sigma_{kk} / \Sigma_{11} \quad \text{EQN. 11}$$

Tissue signals generally exhibit low motion and harmonic energy and therefore a low NSSA; free microbubble signals generally exhibit a large degree of motion and harmonic energy and therefore a high NSSA; and adherent microbubble signals generally exhibit a low degree of motion but higher harmonic energy than tissue signal. In particular, differential motion can be an additional source of separation between tissue and adherent microbubble signal, such as occurring as a result of secondary radiation force interactions between groups of microbubbles during insonation.

Figure 8:
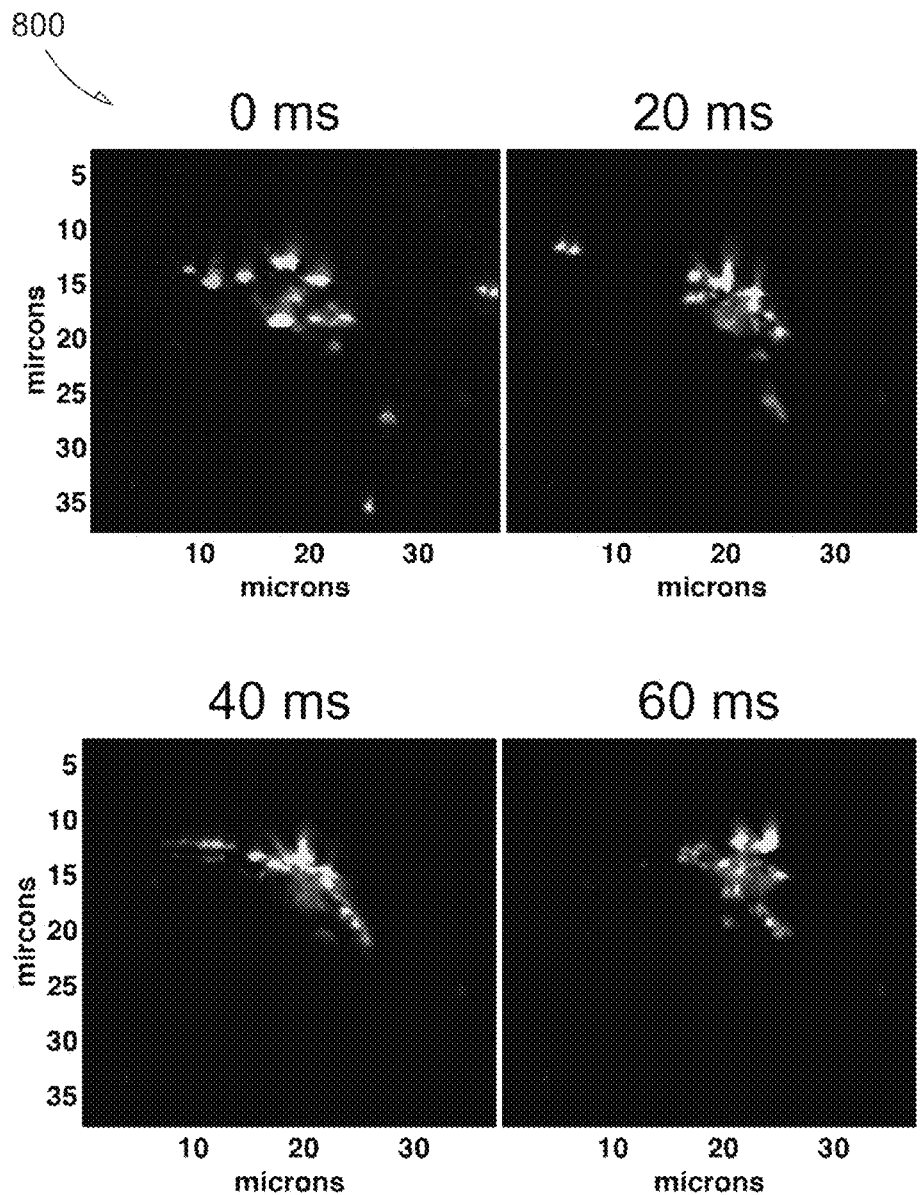
FIG. 8 illustrates generally an illustrative example of experimentally-obtained images obtained using microscopy, such as showing a response of microbubbles to a SiSTM imaging technique.

FIG. 8 illustrates generally an illustrative example 800 of experimentally-obtained images, such as can be obtained using microscopy, such as showing a response of microbubbles to a SiSTM imaging technique.

In the illustrative example of FIG. 8, 2 micrometer (micron) diameter lipid-shelled microbubbles can be imaged while located in a 200-micron-diameter cellulose tube under flow, such as can be acquired using an X71 microscope (Olympus, Center Valley, Pa., USA) and a SIMD24 high speed camera (Specialized Imaging, Simi Valley, Calif., USA) while performing SiSTM imaging using an Ultrasonix RP scanner. In this example, differential motion of the adherent microbubbles were observed due to what was believed to be secondary radiation force effects. As shown in the illustrative example of FIG. 7C, such differential motion can be responsible, at least in part, for a higher NSSA observed from adherent microbubbles versus stationary tissue structures.

Figure 9A:
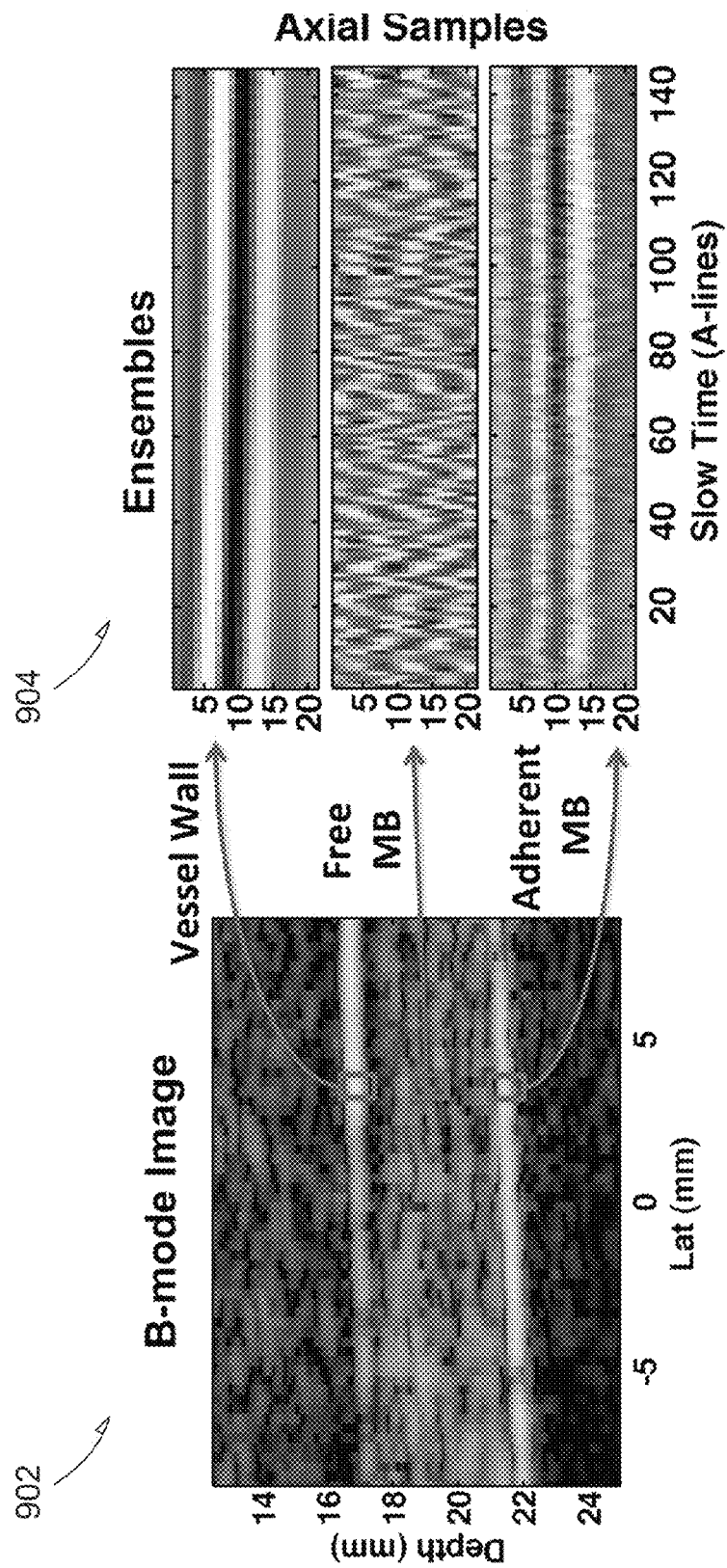
FIG. 9A illustrates generally illustrative examples of imaging information and corresponding ensembles that can be experimentally-obtained from a gelatin phantom including graphite, showing respective representations corresponding to a vessel wall, adherent microbubbles, and free microbubbles.

FIG. 9A illustrates generally illustrative examples of imaging information and corresponding ensembles that can be experimentally-obtained from a gelatin phantom including graphite, showing respective representations corresponding to a vessel wall, adherent microbubbles, and free microbubbles. Graphite can be used to generate speckle. At 902, a B-mode image can be acquired representative of a vessel region to be imaged using a SiSTM technique. Corresponding sets of extracted ensembles are shown at 904, such as representative of regions of the image at 902 corresponding to a vessel wall, free microbubbles, and adherent microbubbles.

Figure 9B:
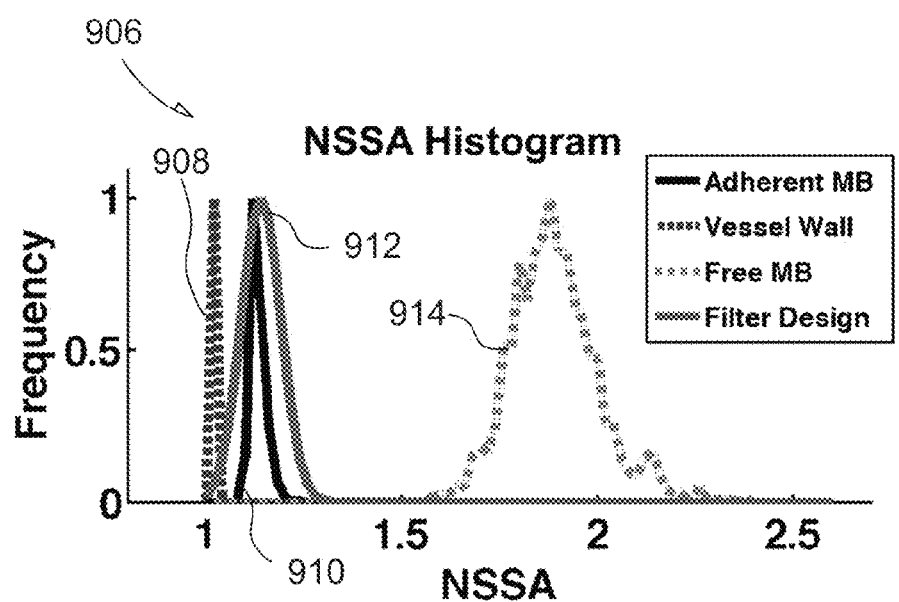
FIG. 9B illustrates generally an illustrative example of a filter weighting that can be identified, such as to isolate a portion of an NSSA corresponding to adherent microbubbles.

FIG. 9B illustrates generally an illustrative example 906 of a filter weighting 912 that can be identified, such as to isolate a portion of an NSSA corresponding to adherent microbubbles 910. Statistical dimensionality and NSSA can be highest for free microbubbles 908, such as followed by adherent microbubbles 910, and an NSSA signature corresponding to a vessel wall 914. The red lines illustrate generally a filter weighting 912 that can be specified, such as to isolate the adherent microbubble signal.

Figure 10A:
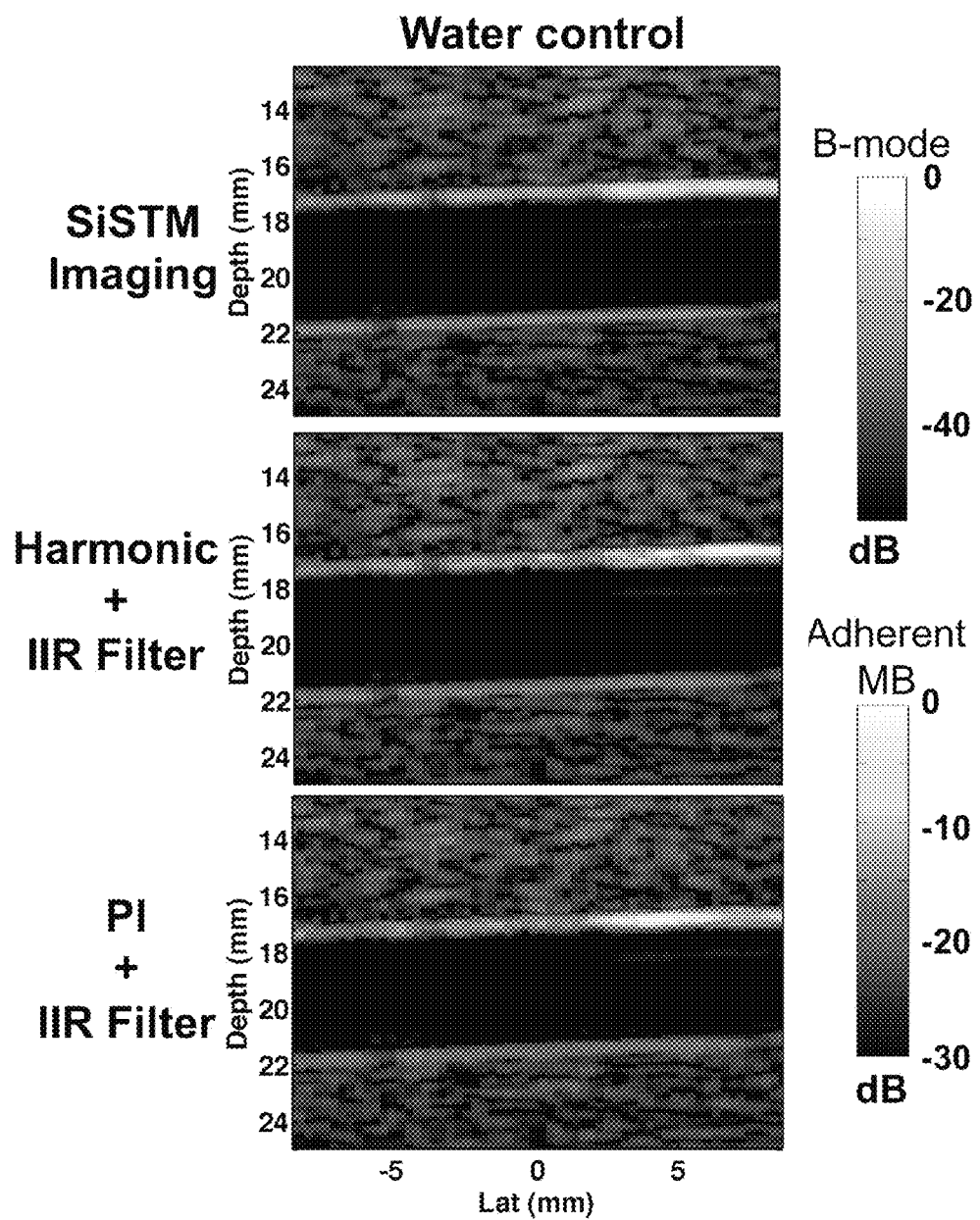
FIGS. 10A and 10B illustrate generally illustrative examples of imaging information that can be experimentally-obtained from a gelatin phantom, such as using various image reconstruction techniques.
Figure 10B:
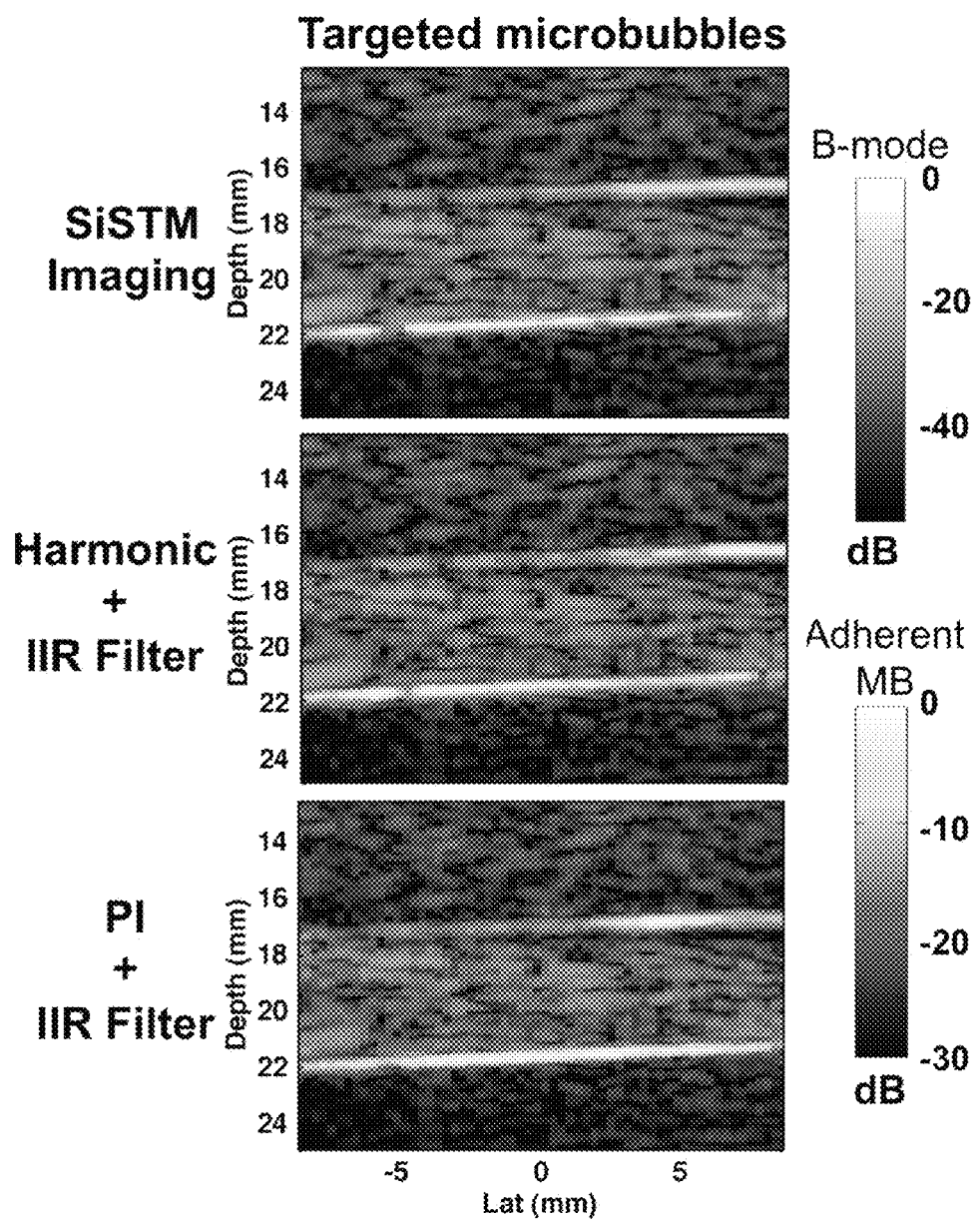

FIGS. 10A and 10B illustrate generally illustrative examples of imaging information that can be experimentally-obtained from a gelatin phantom, such as using various image reconstruction techniques. In FIG. 10A, a filter weighting function can be constructed (e.g., such as similar to the filter weighting 912 of FIG. 9B), having a shape similar to a band pass filter in the frequency domain. For example, a Gaussian window can be used to span a region of NSSA values characteristic of adherent microbubbles. Such a weighting function can be represented by:

$$w_k(\underline{\Sigma}) = e^{-\left(\frac{(NSSA-\mu)^2}{2\sigma^2}\right)}$$  EQN. 12

The filter parameters $\mu$ and $\sigma$ can represent a mean and standard deviation of the filter weighting function, respectively. In SiSTM imaging, the SVF technique can be used to isolate regions of the image corresponding to adherent microbubbles rather than to separate spatially-overlapping signal components. As a result $w_k(\underline{\Sigma})$ need not be a function of k and filtering EQN. 5, discussed above, can amount to a constant weighting applied to an ensemble of interest, $x_{M/2}$.

FIGS. 10A and 10B illustrate generally experimentally-obtained in vitro information, such as can be obtained using gelatin vessel phantoms with a physiologically relevant vessel diameter of about 4 millimeters (mm) and a flow rates of about 2.6 centimeters per second (cm/s). Gelatin phantoms can be constructed according to a Hall technique, and microbubble solutions comprising about $2 \times 10^6$ microbubbles/milliliter (mbbl/mL) of about 2 micron diameter microbubbles can be used. Gelatin phantoms can be coated with avidin or a bovine serum albumin (BSA) blocking agent, such as overnight before obtaining echo information. Avidin-coated gelatin phantom can allow for targeted microbubble imaging while BSA blocked gelatin can provide a controlled experiment where microbubble adhesion can be attributed to non-specific binding only. A second set of controls can be performed with deionized water rather than microbubbles, such as shown in the illustrative example of FIG. 10A.

Imaging shown in FIGS. 10A and 10B can be obtained using the same pulse sequence such that underlying echo data can be equivalent for all techniques shown. In particular, for the SiSTM and Harmonic+IIR methods, received echo data from the first of two pulse inversion pulses can be retained for processing. As shown in FIG. 10B, adherent microbubbles can accumulate on the bottom wall of the vessel due to application of acoustic radiation force pulses. The gray scale background in all images corresponds to a B-mode image while the overlaying 'hot' color map can indicate estimated (e.g., detected) locations of adherent microbubbles from either SiSTM, PI+IIR, or Harmonic+IIR approaches.

Figure 11A:
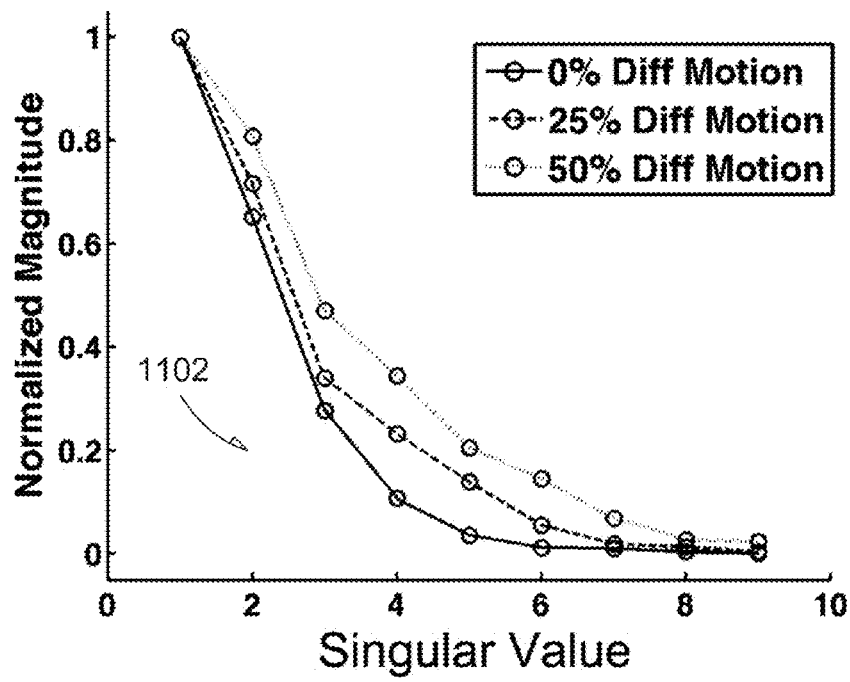
FIG. 11A illustrates generally an illustrative example of singular value spectra that can be obtained at 0%, 25%, and 50% differential motion of underlying acoustic scatterers.
Figure 11B:
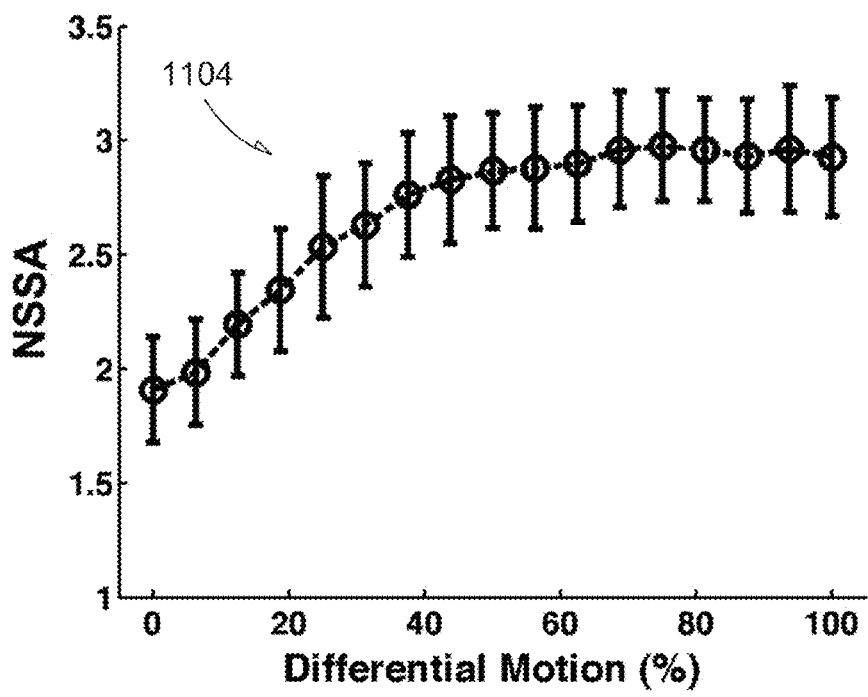
FIG. 11B illustrates generally an illustrative example of a mean singular spectrum area over 100 trials as a function of percent differential motion.

FIG. 11A illustrates generally an illustrative example 1102 of singular value spectra that can be obtained at 0%, 25%, and 50% differential motion of underlying acoustic scatterers and FIG. 11B illustrates generally an illustrative example 1104 of a mean singular spectrum area over 100 trials as a function of percent differential motion.

As discussed above in relation to FIGS. 4A and 4B, respective singular value spectra are generally monotonically related to motion characteristics of the underlying acoustic targets particularly when echo data is complex. FIG. 11A illustrates generally simulation results of the change in a ratio of the first singular value to the sum of singular values versus axial motion and decorrelation. Parameters of the singular value spectrum are also generally monotonic with differential motion at the same mean displacement.

In the illustrative example of FIG. 11A, differential motion can be simulated by such as by assigning a Gaussian probability density function (pdf) to scatterer displacements. For example, a 25% differential motion indicates that the standard deviation to mean displacement ratio of acoustic scatterers can be 1/4. Accordingly, singular value spectra of complex echo data in SVF can be used to estimate motion-based parameters including but not limited to decorrelation, differential motion, shear wave velocity, and displacement.

Moreover, in ultrasound-based targeted molecular imaging, the binding strength of adherent microbubbles to tissue can be revealed in the microbubbles' motion characteristics such as including one or more of decorrelation, differential motion, or displacement. In this manner, a singular value spectrum can be used as a measure of contrast agent binding strength or binding specificity.

SVF techniques are not restricted to extracting motion characteristics or reducing or enhancing signal components based on motion characteristics. Such SVF techniques can be used to extract characteristics of spatial trends or reduce or enhance signal components based on spatial characteristics in an analogous manner. SVF techniques can be used for one or more of reduction of artifact signal in B-mode ultrasound imaging; reduction of displacement estimation bias in any medical imaging technique that uses obtained reflected or transmitted energy information data to quantify motion, such as medical ultrasound, optical or laser-based elastography, or X-ray imaging; reduction of displacement estimation bias of physiological tissue, in vivo.; photoacoustic, optical or laser-based, or ultrasound-based targeted molecular imaging including one or more of estimation of binding specificity; or targeted imaging of contrast agents such as microbubbles, carbon nanorods, liposomes, gadolinium, lipoproteins, superparamagnetic iron oxide magnetic nanoparticles for MR imaging; determination of one or more characteristics such as echo decorrelation, differential motion; displacement, velocity; estimation of blood velocity or perfusion in a patient; acoustic radiation force imaging; shear wave imaging; or elastography.

VARIOUS NOTES & EXAMPLES

Each of the non-limiting examples discussed in this document can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system for use with a transducer array, the transducer array configured to deliver energy to a tissue region, the system comprising:
    a processor circuit configured to:
        obtain, using the transducer array, information indicative of the delivered energy reflected from the tissue region;
        form respective input matrices representative of the obtained information indicative of the energy reflected from the tissue region, the respective input matrices including information corresponding to a spatial dimension and a temporal dimension, the input matrices respectively comprising an ensemble-of-interest and at least one ensemble corresponding to a spatial location nearby a spatial location corresponding to the ensemble-of-interest;
        perform respective singular value decompositions on the respective input matrices to obtain respective sets of singular values corresponding to respective sets of singular vectors;
        obtain respective output matrices including weighting a respective projection of a respective ensemble-of-interest onto at least one of the singular vectors included in a respective set of singular vectors; and
        using the respective output matrices, at least one of determine a characteristic, or construct an image, of at least a portion of the tissue region.

2. The system of claim 1, wherein the processor circuit is configured to obtain a respective output matrix including using an adaptively determined weighting function.

3. The system of claim 2, wherein the processor circuit is configured to adaptively determine at least one respective weighting function for each respective output matrix, each respective output matrix corresponding to a respective input matrix.

4. The system of claim 2, wherein the weighting function varies continuously between 0 and 1 without a discontinuity.

5. The system of claim 4, wherein the weighting function includes a modified sigmoidal weighting function.

6. The system of claim 2, wherein the weighting function is adaptively determined using information about at least one of the respective singular values.

7. The system of claim 2, wherein the weighting function is adaptively determined at least in part using information about a motion complexity of a target in the tissue region.

8. The system of claim 2, wherein the weighting function is adaptively determined to suppress or eliminate at least one of a clutter artifact or noise.

9. The system of claim 1, wherein the processor circuit is configured to determine a characteristic at least a portion of the tissue region using the respective output matrices.

10. The system of claim 9, wherein the characteristic includes a motion of a target located within the tissue region.

11. The system of claim 1, wherein the ensemble-of-interest includes information corresponding to a depth dimension with respect to a transducer plane and a temporal dimension.

12. The system of claim 1, wherein the processor circuit is configured to construct an image of at least a portion of the tissue region using the respective output matrices.

13. The system of claim 12, wherein the respective ensembles-of-interest correspond to respective pixels included in an image frame; and
wherein the processor circuit is configured to construct the image by determining a filtered output matrix corresponding to respective pixels in the image frame using the respective weightings and the respective singular value decompositions.

14. The system of claim 1, wherein the obtained information includes complex-valued samples of the echo information represented by real and imaginary parts; and
wherein the respective input matrices comprise complex-valued elements represented by real and imaginary parts.

15. The system of claim 1, further comprising an ultrasonic transducer array configured to insonify the region of tissue using ultrasonic energy; and
wherein the obtained information indicative of the energy reflected from the tissue region comprises ultrasonic energy reflected from the insonified region.

16. A system for use with a transducer array, the transducer array configured to deliver energy to a tissue region, the system comprising:
a processor circuit configured to:
obtain, from the transducer array, information indicative of the delivered energy reflected from the tissue region;
form respective input matrices representative of the obtained information indicative of the energy reflected from the tissue region, the respective input matrices including information corresponding to a spatial dimension and a temporal dimension, the input matrices respectively comprising an ensemble-of-interest and at least one ensemble corresponding to a spatial location nearby a spatial location corresponding to the ensemble-of-interest;
perform respective singular value decompositions on the respective input matrices to obtain respective sets of singular values corresponding to respective sets of singular vectors;
obtain respective output matrices including weighting a respective projection of a respective ensemble-of-interest onto at least one of the singular vectors included in a respective set of singular vectors using a weighting function, including adaptively determining the weighting function using information about at least one of the respective singular values; and
using the respective output matrices, at least one of determine a characteristic, or construct an image, of at least a portion of the tissue region;
wherein the weighting function:
varies continuously between 0 and 1 without a discontinuity;
and
includes a modified sigmoidal weighting function.

17. A method, comprising:
obtaining, from a transducer array, information indicative of the delivered energy reflected from the tissue region;
forming respective input matrices representative of the obtained information indicative of the energy reflected from the tissue region, the respective input matrices including information corresponding to a spatial dimension and a temporal dimension, the input matrices respectively comprising an ensemble-of-interest and at least one ensemble corresponding to a spatial location nearby a spatial location corresponding to the ensemble-of-interest;
performing respective singular value decompositions on the respective input matrices to obtain respective sets of singular values corresponding to respective sets of singular vectors;
obtaining respective output matrices including weighting a respective projection of a respective ensemble-of-interest onto at least one of the singular vectors included in a respective set of singular vectors; and
using the respective output matrices, at least one of determining a characteristic, or constructing an image, of at least a portion of the tissue region.

18. The method of claim 17, comprising obtaining a respective output matrix including weighting the respective projection using a weighting function using an adaptively determined weighting function.

19. The method of claim 18, comprising adaptively determining at least one respective weighting function for each respective output matrix, each respective output matrix corresponding to a respective input matrix.

20. The method of claim 18, wherein the weighting function varies continuously between 0 and 1 without a discontinuity.

* * * * *

UNITED STATES PATENT AND TRADEMARK OFFICE
CERTIFICATE OF CORRECTION

PATENT NO.        : 9,002,080 B2                         Page 1 of 1
APPLICATION NO.   : 13/650821
DATED             : April 7, 2015
INVENTOR(S)       : Mauldin, Jr. et al.

It is certified that error appears in the above-identified patent and that said Letters Patent is hereby corrected as shown below:

Specification
In column 1, line 16-19, delete, "This invention was made with government support under R01EB001826 awarded by the National Institutes of Health (NIH).," and insert --This invention was made with government support under EB018262, EB002185, RR027333 awarded by the National Institutes of Health.--, therefor Signed and Sealed this
Seventeenth Day of May, 2016

Michelle K. Lee
*Director of the United States Patent and Trademark Office*